United States Patent

Haning et al.

[11] Patent Number: 5,989,532
[45] Date of Patent: Nov. 23, 1999

[54] HAIR TREATMENT COMPOSITION AND METHOD

[75] Inventors: Linda J. Haning, Prior Lake; Coreen Ann Johnson, Inver Grove Heights, both of Minn.

[73] Assignee: Bristol-Myers Squibb Company, New York, N.Y.

[21] Appl. No.: 08/979,709

[22] Filed: Nov. 27, 1997

[51] Int. Cl.⁶ .................................................. A61K 7/075
[52] U.S. Cl. ............................................................ 424/70.1
[58] Field of Search .............................................. 424/70.1

[56] References Cited

U.S. PATENT DOCUMENTS

| | | | |
|---|---|---|---|
| 4,183,366 | 1/1980 | Bartuska et al. | 132/7 |
| 4,873,079 | 10/1989 | Hahn | 424/70 |
| 4,938,954 | 7/1990 | Gross et al. | 424/71 |
| 4,992,077 | 2/1991 | Tennigkeit et al. | 8/406 |
| 5,006,127 | 4/1991 | Tennigkeit et al. | 8/406 |
| 5,059,414 | 10/1991 | Dallal et al. | 424/70 |
| 5,205,837 | 4/1993 | Andrean et al. | 8/405 |
| 5,482,703 | 1/1996 | Pings . | |
| 5,679,114 | 10/1997 | Haning et al. | 8/405 |

FOREIGN PATENT DOCUMENTS 2149806  6/1985  United Kingdom .

*Primary Examiner*—S. Mark Clardy
*Assistant Examiner*—Michael A. Williamson
*Attorney, Agent, or Firm*—Morton S. Simon; Charles J. Zeller; Thomas R. Savitsky

[57] ABSTRACT

A hair treatment composition comprising a mixture of polyvinylpyrrolidone and a member selected from the group consisting of an ethoxylated triglyceride, a quaternary ammonium chloride, phenyl trimethicone, an acrylate containing polymer and dimethicone copolyol ester and mixtures thereof, provided that the weight ratio of the polyvinylpyrrolidone to the ethoxylated triglyceride is greater than about 7:1 and the weight ratio of the polyvinylpyrrolidone to the acrylate containing polymer is greater than about 7:1 is described herein.

11 Claims, No Drawings

HAIR TREATMENT COMPOSITION AND METHOD

BACKGROUND OF THE INVENTION

1. Field of the Invention.

The present invention deals with hair care products. In particular, the present invention deals with hair care products for treatment of the hair upon the scalp, and particularly products to impart desirable texture and body to the hair while avoiding a condition commonly known as the "frizzes". The present invention deals with hair products which are substantive to the hair and which are intended to be left upon the hair after application. The product of the present invention permits a single product to be used to achieve conditioning and a gel type fixative in one operation typically following towel drying of the hair (to a damp condition).

2. Description of the Art Practices.

Various products are known for use in treating the hair. For instance, Pings in U.S. Pat. No. 5,482,703 issued Jan. 9, 1996 teaches hair care products which are utilized to treat the hair and then removed from the hair. The Pings patent discloses the use of polydimethyl siloxane, a lipid vehicle, a cationic surfactant material and a dimethicone copolyol.

Gross, et. al., in U.S. Pat. No. 4,938,954, issued Jul. 3, 1990, describes hair wax compositions containing polyethylene glycol, a hydrogenated castor oil which is ethoxylated, glycerol or ethyl hexane diol, and/or a lower molecular weight polyethylene glycol, and water.

Pemulen™ polymeric emulsifiers bulletin P0048 bearing a date of Apr. 26, 1995 discloses certain formulations pertaining to the present invention. The Pemulen™ polymeric emulsifiers bulletin P0048 utilizes animal derived ingredients while the products of the present invention are free of animal derived products.

To the extent that the foregoing references are applicable to the present invention they are herein specifically incorporated by reference. Throughout the specification and claims, percentages and ratios are by weight unless otherwise indicated. Temperatures given herein are degrees Celsius unless otherwise indicated.

SUMMARY OF THE INVENTION

The present invention describes a hair treatment composition comprising: a mixture of polyvinylpyrrolidone and a member selected from the group consisting of an ethoxylated triglyceride, a quaternary ammonium chloride, phenyl trimethicone, an acrylate containing polymer and dimethicone copolyol ester and mixtures thereof, provided that the weight ratio of the polyvinylpyrrolidone to the ethoxylated triglyceride is greater than about 7:1 and the weight ratio of the polyvinylpyrrolidone to the acrylate containing polymer is greater than about 7:1.

A further aspect of the present invention is a hair treatment composition comprising: a mixture of ethoxylated triglyceride and a member selected from the group consisting of a phenyl trimethicone, and a dimethicone copolyol ester and mixtures thereof provided that the phenyl trimethicone to ethoxylated triglyceride weight ratio is less than about 9:1.

Yet a further aspect of the present invention is a hair treatment composition comprising: a mixture of quaternary ammonium chloride and a member selected from the group consisting of phenyl trimethicone, and a dimethicone copolyol ester and mixtures thereof provided that the quaternary ammonium chloride to phenyl trimethicone weight ratio is less than about 1:5.

An additional aspect of the present invention is a hair treatment composition comprising: a mixture of phenyl trimethicone and a member selected from the group consisting of an acrylate containing polymer and a dimethi-cone copolyol ester and mixtures thereof provide that the phenyl trimethicone to acrylate containing polymer weight ratio is less than 8:1.

Also described herein is a method of utilizing the compositions of the present invention to treat the hair upon the scalp to condition the hair upon the scalp to provide texture and body including the steps of contacting the hair upon the scalp with a composition comprising: a mixture of polyvinylpyrrolidone and a member selected from the group consisting of an ethoxylated triglyceride, a quaternary ammonium chloride, phenyl trimethicone, an acrylate containing polymer and dimethicone copolyol ester and mixtures thereof, to change the texture and body of the hair upon the scalp thereby conditioning the hair provided that the weight ratio of the polyvinylpyrrolidone to the ethoxylated triglyceride is greater than about 7:1 and the weight ratio of the polyvinylpyrrolidone to the acrylate containing polymer is greater than about 7:1.

DETAILED DESCRIPTION OF THE INVENTION

The first component of the present invention is the polyvinylpyrrolidone. The polyvinylpyrrolidone may be obtained from any convenient source. The preferred source of the polyvinylpyrrolidone is BASF of Wyandotte, Michigan. The polyvinylpyrrolidone is typically utilized in the formulations of the present invention at level of 2 to 8 percent by weight of the finished formulation (including water), preferably 2.25 to 7 percent percent by weight of the finished formulation, and most preferably 2.5 to 5 percent by weight of the finished formulation.

The second component of the present invention is a quaternary ammonium chloride which is a quaternary cationic surfactants. Examples of such cationic surfactants include tricetyl methyl ammonium chloride, cetyl trimethyl ammonium chloride, stearyldi-methyl benzyl ammonium chloride, and di-(partially hydrogenated tallow) dimethylammonium chloride.

A preferred cationic surfactant is a linoleamidopropyl PG-dimonium chloride phosphate. The PG indicates that the product is reacted with propylene glycol to give a product having the formula $[RC=ONH(CH_2)_3N(CH_3)_2CH_2CHOHCH_2O]^+-[P=O]$ $3Cl^-$, such that the preferred cationic materials have a phosphate functionality.

The cationic surfactant is typically utilized in the formulations of the present invention at level of 0.1 to 8 percent by weight of the finished formulation (including water), preferably 0.15 to 5 percent by weight of the finished formulation, and most preferably 0.2 to 2.5 percent by weight of the finished formulation.

The third component of the present invention is a phenyl trimethicone. The phenyl trimethicone component of the present invention is a silicone based component. The phenyl trimethi-cone component is typically utilized in the formulations of the present invention at level of 0.25 to 2.0 percent by weight of the finished formulation (including water), preferably 0.50 to 1.75 percent by weight of the finished formulation, and most preferably 0.75 to 1.25 percent by weight of the finished formulation.

The fourth component of the present invention is an acrylate containing polymer. The acrylate containing polymer is typically a cross polymer. The preferred cross polymers are described as C10-30 alkyl acrylate cross polymers.

The acrylate containing polymer component is typically utilized in the formulations of the present invention at level of 0.05 to 2.0 percent by weight of the finished formulation (in-cluding water), preferably 0.10 to 1.00 percent by weight of the finished formulation, and most preferably 0.15 to 0.75 percent by weight of the finished formulation.

The fifth component of the present invention is a dimethicone copolyol ester available The Fanning Corporation 2450 West Hubbard Street Chicago, Ill. 60612-1408. A preferred dimethicone copolyol ester is that made with Meadowfoam oil. The reaction to form the dimethicone copolyol ester is esterification. In the esterification reaction of the dimethi-cone copolyol and Meadowfoam oil a distribution of reaction products is to be expected.

Typically, in the esterification reaction of the dimethicone copolyol and Meadowfoam oil about at least 90% of all of the hydroxyl groups in the reactant are esterified. The products from the esterification of the reactant are the monoester, the diester, the triester, and the tetraesters of the reactant. The dimethicone copolyol ester (preferably the meadowfoamate) is incorporated into the product as a 100% active ingredient. The dimethicone copolyol ester is typically utilized in the formulations of the present invention at level of 0.25 to 5.0 percent by weight of the finished formulation (including water), preferably 0.5 to 3.00 percent by weight of the finished formulation, and most preferably 0.75 to 1.75 percent by weight of the finished formulation.

PRODUCT RATIOS

The products of the present invention perform for their intended conditioning purpose as previously described. However, the products in the formulation perform in a superior manner when they are utilized in a preferred range.

For instance, the weight ratio of the polyvinylpyrrolidone to the ethoxylated triglyceride is greater than about 7:1 and preferably greater than 8:1 and more preferably greater than 9:1. The weight ratio of the polyvinylpyrrolidone to the acrylate containing polymer is greater than about 7:1, and preferably greater than 8:1 and more preferably greater than 9:1.

The phenyl trimethicone to ethoxylated triglyceride weight ratio is less than about 9:1, preferably less than 8:1 and most preferably less than 7:1. The weight ratio of the quaternary ammonium chloride to phenyl trimethicone is less than about 1:5, preferably less than 1:4 and most preferably less than 2:5. The phenyl trimethicone to acrylate containing polymer weight ratio is less than 8:1, preferably less than 6:1, and most preferably less than 5:1.

OPTIONAL INGREDIENTS

The products described herein can contain a variety of nonessential optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea.

Additional ingredients include thickeners and viscosity modifiers such as a diethanolamide of a long chain fatty acid (e.g., PEG 3 lauramide) cocomonoethanolamide, amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

PRODUCT PREPARATION

The product is prepared by combining the various ingredients in a suitable mixing vat. Water is added to the vat and stirring is initiated. The ethoxylated triglyceride and quaternary ammonium chloride are added to the water.

In a separate mixing vat the phenyl trimethicone and acrylate containing polymer are mixed together at the ambient temperature. Following mixing of the phenyl trimethicone and acrylate containing polymer these materials are mixed into the vat containing the water and the ethoxylated triglyceride with the resulting mixture heated to 50° C.

The dimethicone copolyol ester is then added, with mixing, to the combined mixture of the phenyl trimethicone, the acrylate containing polymer, the water, the ethoxylated triglyceride and the quaternary ammonium chloride. The stirring continues until the product mixing is complete usually about one hour.

Any remaining ingredients, including preservatives, fragrances and anti microbial materials may be added at any point in the process where the added ingredient maintains its intended function and where the added ingredient does not interfere with the remainder of the product.

What follows is an example of the preparation of the composition of the present invention:

EXAMPLE I

The composition of the present invention is prepared by adding deionized water to a mixing vat. Mixing is initiated, and the following components are combined as described above:

| Component | percent by weight |
| --- | --- |
| Polyvinylpyrrolidone | 3.00 |
| Sodium hydroxymethylglycinate | 0.40 |
| Tetrasodium EDTA | 0.05 |
| PEG-60 Almond Glyceride | 0.20 |
| Linoleamidopropyl PG-Dimonium Chloride Phosphate | 0.30 |
| Phenyl Trimethicone | 1.00 |
| Acrylates/C10–30 Alkyl Acrylate Cross Polymer | 0.25 |
| Dimethicone Copolyol Meadowfoamate | 1.00 |
| Deionized water | balance to 100 parts |

EXAMPLE II

The composition of the present invention is prepared by adding deionized water to a mixing vat. Mixing is initiated, and the following components are combined as described above:

| Component | percent by weight |
| --- | --- |
| Polyvinylpyrrolidone | 3.00 |
| Sodium hydroxymethylglycinate | 0.40 |
| Tetrasodium EDTA | 0.05 |
| PEG-60 Almond Glyceride | 0.10 |
| Linoleamidopropyl PG-Dimonium Chloride Phosphate | 0.30 |
| Phenyl Trimethicone | 0.10 |
| Acrylates/C10–30 Alkyl Acrylate Cross Polyymer | 0.50 |
| Dimethicone Copolyol Meadowfoamate | 1.00 |
| Deionized water | balance to 100 parts |

PRODUCT UTILIZATION

The level of application of the product dispensed as an aqueous liquid dispersion or solution to the weight of the dry hair on the scalp to be treated is about 0.01 to 0.75 grams per gram of dry hair.

The product is applied to clean hair upon the scalp, preferably following a thorough cleansing of the hair. For the best results it is suggested that the hair be wet when the product is applied. The hair may be washed with a surfactant as described below.

The product is conveniently applied to the hair at room temperature to slightly elevated temperatures, e.g. 18 to 38 degrees Celsius. A fixative hair spray may be applied to the scalp hair so treated according to the present invention. Suitable fixative hair sprays include PVM MA (polyvinyl methacrylate maleic anhydride copolymer) in SD 40 alcohol.

Suitable surfactants (detergents) for cleaning the hair on the scalp prior to applying the composition of the present invention are described below. The same surfactant materials will remove the product of the invention from the hair on the scalp.

Suitable anionic surfactants are those generally incorporated into a shampoo product. Generally, the anionic surfactant is a water-soluble alkyl or alkyl aryl sulfonate having from about 8 to about 22 carbons, preferably from about 12 to about 18 carbons, in the alkyl radical, which may be straight or branched chain, and also includes such classes of compounds ethoxylated with from 1 to 5 mols, preferably 1 to 3 mols, ethylene oxide per molecule. The sulfate or sulfonate group is typically base-neutralized to provide an alkali metal, especially sodium or potassium, ammonium, or mono, di-, or trialkanolium cation.

Illustrative anionic surfactants of the above-named classes include: Sodium cetyl sulfate, sodium myristyl sulfate, sodium lauryl sulfate, sodium tallow sulfate, sodium decyl sulfate, sodium decylbenzene sulfonate, sodium tridecylbenzene sulfonate, sodium C 14 to C 16 olefin sulfonate, sodium C 12 to C 15 alcohol sulfate, sodium lauryl ether sulfate, sodium myristyl ether sulfate, sodium polyoxyethylene (5 mols ethylene oxide) lauryl ether sulfate, sodium polyoxyethylene (12 mols ethylene oxide) lauryl ether sulfate, sodium nonylphenyl ether sulfate, sodium polyoxyethylene (1 to 4 mols ethylene oxide), C 12 to C 15 alkyl ether sulfate, sodium lauryl sulfoacetate.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized. Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight C 12–13 compounds; from 60 to 100% by weight of C 14–15–16 compounds, from about 0 to 20% by weight of C 17–18–19 compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Other suitable anionic detergents utilizable herein are olefin sulfonates having about 12 to about 24 carbon atoms. The term "olefin sulfonates" is used herein to mean compounds which can be produced by the sulfonation of an alpha-olefin by means of uncomplexed sulfur trioxide, followed by neutralization of the acid reaction mixture in conditions such that any sultones which have been formed in the reaction are hydrolyzed to give the corresponding hydroxy-alkane sulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefin from which the olefin sulfonates are derived are mono-olefin having 12 to 24 carbon atoms, preferably 14 to 16 carbon atoms. Preferably, they are straight chain olefin. Examples of suitable 1-olefin include 1-dodecene; 1-tetradecene; 1-hexadecene; 1-octadecene; 1-cicosene and 1-tetra-eosene.

Additional surfactant materials which may be utilized herein include the following exemplified materials. Long Chain tertiary amine oxides corresponding to the following general formula:

$$R^1R^2R^3NO$$

wherein $R^1$ contains an alkyl, alkenyl or monohydroxy alkyl radical of from about 8 to about 18 carbon atoms, from 0 to about 10 ethylene oxide moieties, and from 0 to 1 glyceryl moiety, and $R^2$ and $R^3$ contain from 1 to about 3 carbon atoms and from 0 to about 1 hydroxy group, e.g., methyl, ethyl, propyl, hydroxy ethyl, or hydroxy propyl radicals. The arrow in the formula is omitted as it is a conventional representation of a semi-polar bond between the nitrogen and the oxygen.

Examples of amine oxides suitable for use in this invention include dimethyldodecyl-amine oxide, oleyldi(2-hydroxyethyl)amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxy-ethyldimethylamine oxide, 3-dodecoxy-2-hydroxypropyldi (3-hydroxy-propyl) amine oxide, and dimethyl-hexadecylamine oxide.

Further additional surfactants include long chain tertiary phosphine oxides corresponding to the following general formula:

$$RR'R''PO$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and r' and r'' are each alkyl or monohydroxyalkyl groups containing from 1 to 3 carbon atoms. The arrow in the formula is omitted as it is a conventional representation of a semi-polar bond between the phosphorus and the oxygen.

Having described the invention, the following is claimed:

1. A hair treatment composition comprising:
   a mixture of polyvinylpyrrolidone, an ethoxylated triglyceride, a quaternary ammonium chloride, phenyl trimethicone, an acrylate containing polymer and dimethicone copolyol ester, each ingredient present in a cosmetically effective amount.

2. The hair treatment composition of claim 1 wherein the weight ratio of the polyvinylpyrrolidone to the ethoxylated triglyceride is greater than about 7:1.

3. The hair treatment composition of claim 1 wherein the weight ratio of the polyvinylpyrrolidone to the acrylate containing polymer is greater than about 7:1.

4. The hair treatment composition of claim 3 wherein the weight ratio of the polyvinylpyrrolidone to the ethoxylated triglyceride is greater than about 7:1.

5. The composition of claim 1 further including water.

6. A method of treating hair upon the scalp to condition the hair upon the scalp to provide texture and body including the steps of contacting the hair upon the scalp with a composition comprising:
   a mixture of polyvinylpyrrolidone an ethoxylated triglyceride, a quaternary ammonium chloride, phenyl trimethicone, an acrylate containing polymer and dimethicone copolyol ester, each ingredient present in a cosmetically effective amount, to change the texture and body of the hair upon the scalp thereby conditioning the hair.

7. The method of claim 6 further including the step of washing the hair with a surfactant prior to applying said composition to the hair and/or including the step of applying the composition to the hair while the hair is damp.

8. The method of claim 6 further including the step of treating the hair with a fixative spray after applying the composition to the hair.

9. The method of claim 6 wherein the weight ratio of the polyvinylpyrrolidone to the ethoxylated triglyceride is greater than about 7:1.

10. The method of claim 6 wherein the weight ratio of the polyvinylpyrrolidone to the acrylate containing polymer is greater than about 7:1.

11. The method of claim 10 wherein the weight ratio of the polyvinylpyrrolidone to the ethoxylated triglyceride is greater than about 7:1.

* * * * *